United States Patent
Yoon

(10) Patent No.: US 6,546,933 B1
(45) Date of Patent: Apr. 15, 2003

(54) OCCLUSION APPARATUS AND METHOD FOR NECROTIZING ANATOMICAL TISSUE STRUCTURES

(76) Inventor: InBae Yoon, 11886 Farside Rd., Ellicott City, MD (US) 21042

(\*) Notice: Subject to any disclaimer, the term of this patent is extended or adjusted under 35 U.S.C. 154(b) by 83 days.

(21) Appl. No.: 09/606,242

(22) Filed: Jun. 29, 2000

(51) Int. Cl.[7] ............................................. A61B 19/00
(52) U.S. Cl. ................................................ 128/898
(58) Field of Search ............................. 128/898, 828, 128/829, 830

(56) References Cited

U.S. PATENT DOCUMENTS

| | | | | |
|---|---|---|---|---|
| 5,026,379 A | * | 6/1991 | Yoon | 606/141 |
| 5,217,473 A | * | 6/1993 | Yoon | 606/157 |
| 5,226,908 A | * | 7/1993 | Yoon | 606/141 |
| 5,334,209 A | * | 8/1994 | Yoon | 606/141 |
| 6,002,968 A | * | 12/1999 | Edwards | 607/101 |
| 6,024,743 A | * | 2/2000 | Edwards | 606/42 |
| 6,159,207 A | * | 12/2000 | Yoon | 606/42 |
| 6,277,089 B1 | * | 8/2001 | Yoon | 604/1 |

\* cited by examiner

*Primary Examiner*—John J. Calvert
*Assistant Examiner*—Alissa L. Hoey
(74) *Attorney, Agent, or Firm*—Law Offices of Royal W. Craig

(57) ABSTRACT

An occlusion apparatus necrotizes an anatomical tissue structure which is disposed in a living body and has a plurality of vessels extending therefrom. The occlusion apparatus includes an elongated tubular member and an occluding mechanism. The tubular member extends along a central longitudinal axis to define a lumen and has a distal end positioned interiorly of the living body and a proximal end disposed opposite the distal end and positioned exteriorly of the living body. The occluding mechanism is operative at the distal end of the tubular member and includes a pair of occluding elements disposed opposite one another. The pair of occluding elements are moveable to and between an opened state and a closed state. In the opened state, the vessels to be occluded are received between the pair of occluding elements. In the closed state, the pair of occluding elements contact and occlude the vessels, thereby necrotizing the anatomical tissue structure. A method necrotizes the anatomical tissue structure and includes the steps of locating the anatomical tissue structure to be necrotized and the vessels extending therefrom, and occluding the vessels to prevent fluid flow into and out of the anatomical tissue structure, thereby causing ischemic necrosis of the anatomical tissue structure.

14 Claims, 7 Drawing Sheets

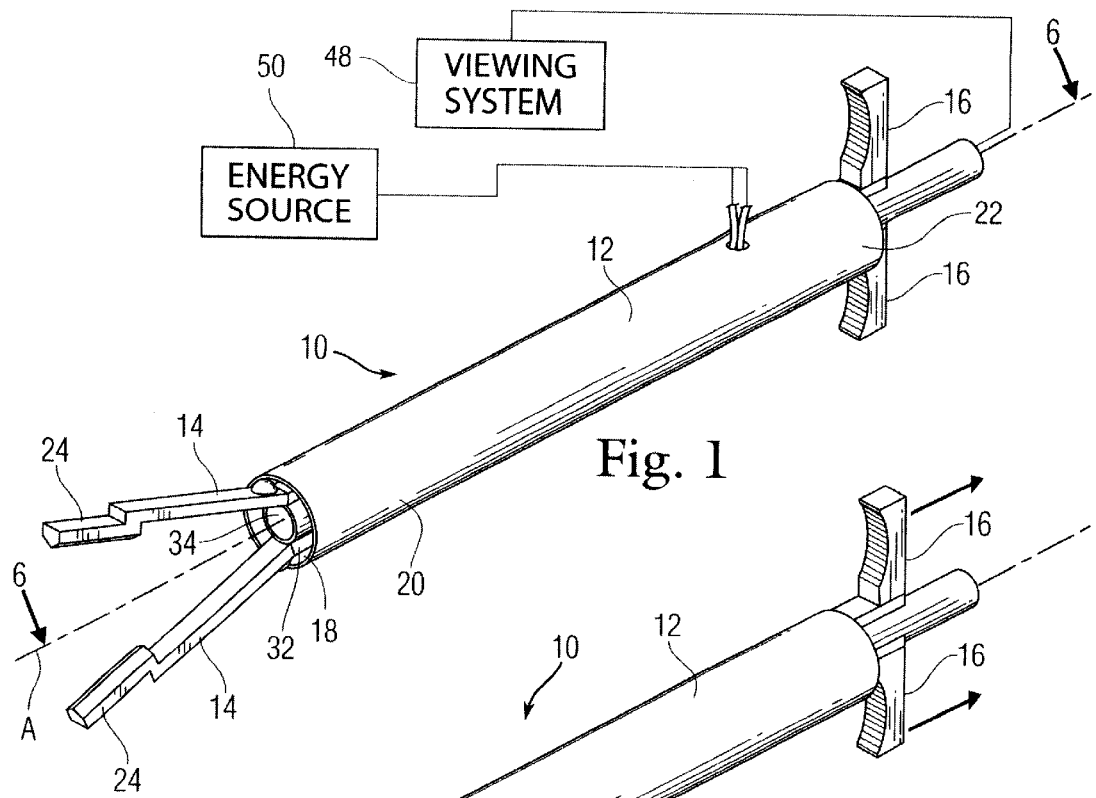
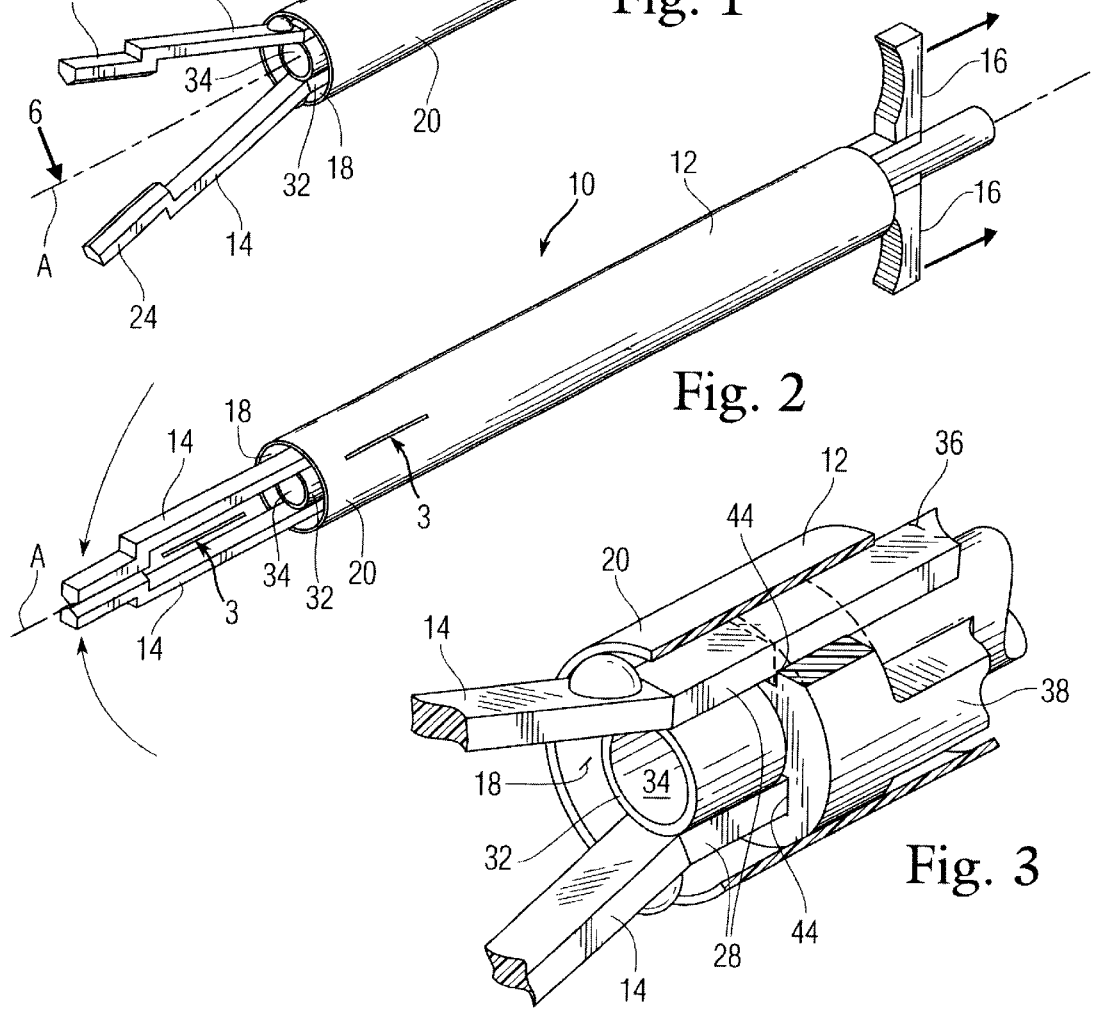

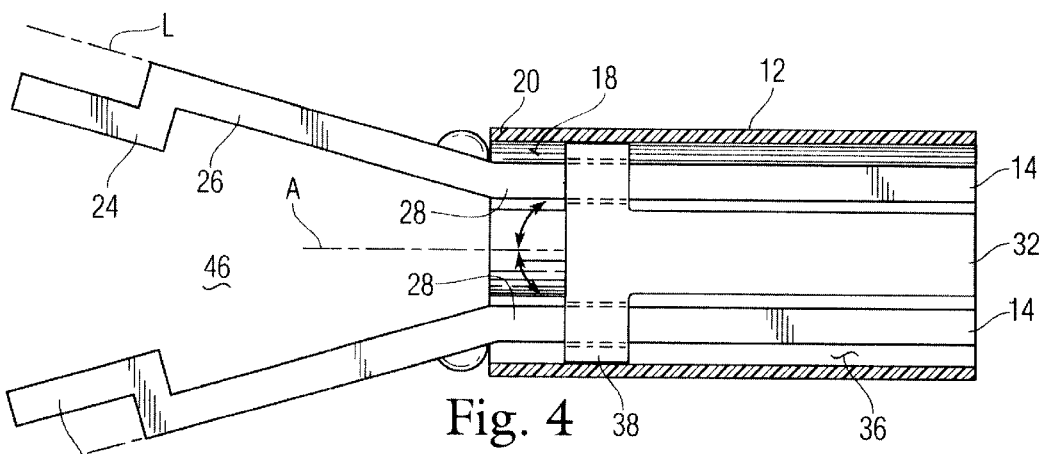
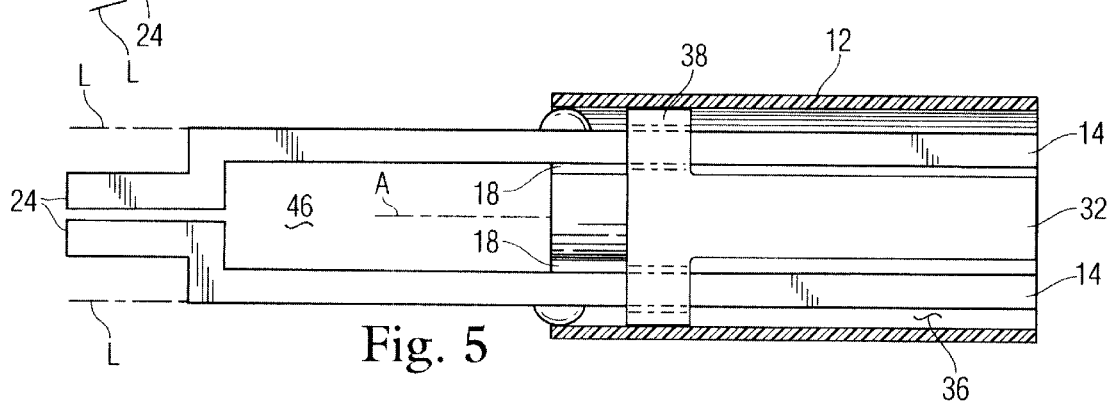
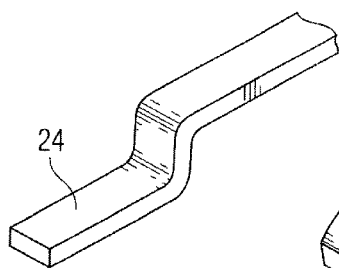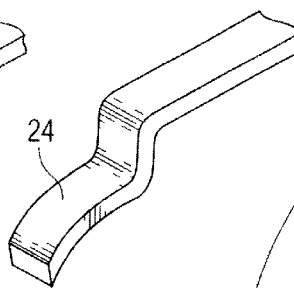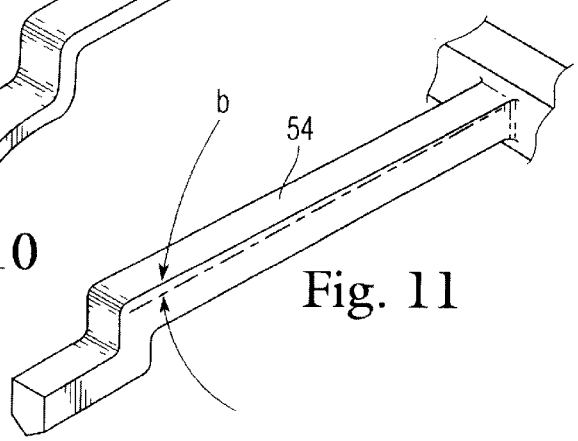
Fig. 9    Fig. 10    Fig. 11

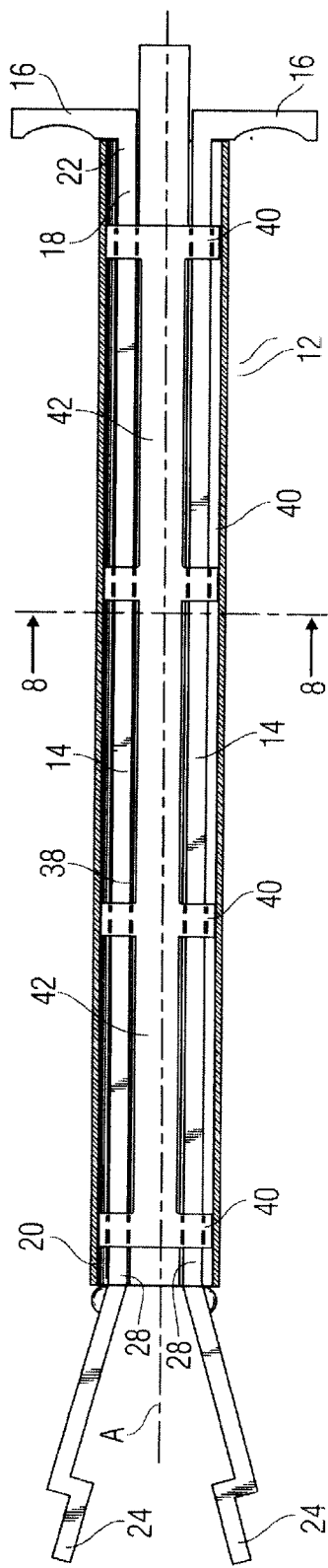
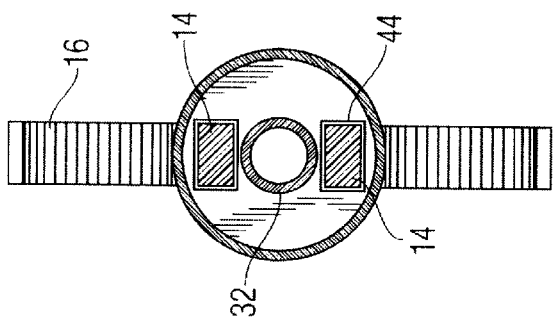
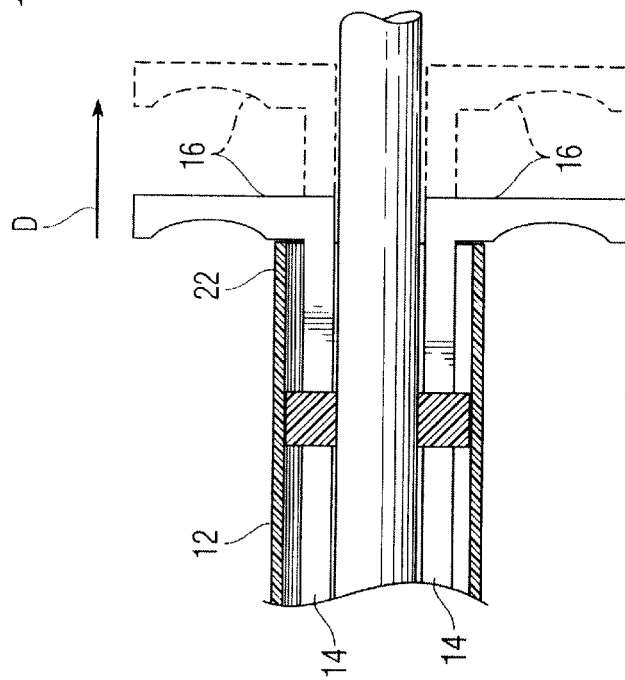
Fig. 6
Fig. 8
Fig. 7

OCCLUSION APPARATUS AND METHOD FOR NECROTIZING ANATOMICAL TISSUE STRUCTURES

FIELD OF THE INVENTION

The present invention relates to a surgical apparatus and method that are used for necrotizing anatomical tissue structures. More particularly, the present invention is directed to a surgical apparatus and method that occludes vessels extending from anatomical tissue structures to cause necrosis of the same.

BACKGROUND OF THE INVENTION

A hysterectomy is surgical removal of the uterus resulting in sterility of a female. Typically, hysterectomies may be performed through an abdominal incision, commonly referred to as an abdominal hysterectomy, or through a vaginal incision, commonly referred to as a vaginal hysterectomy. The uterus can be completely removed or partially removed. Also, the uterus can be removed with the fallopian tubes and ovaries. Hysterectomies may be performed to correct physical ailments in females, such as chronic infection, inflammation of the uterine lining, removal of uterine fibroids and cancer, and correction of chronic vaginal bleeding.

Although most patients recover completely from a hysterectomy procedure, convalescence can be rather lengthy. An average hospital stay can be from five to seven days. Complete recovery may require two weeks to two months. Typically, recovery from a vaginal hysterectomy is faster than an abdominal hysterectomy. Further, like any other surgical procedure, risks are involved. Particularly, risks for a hysterectomy include bleeding and infection. There is also risk associated with anesthesia, such as reaction to the anesthesia as well as problems with breathing.

It would be beneficial to provide a patient with an alternative surgical procedure to a hysterectomy. It would be advantageous to the patient to provide such an alternative surgical procedure that would reduce hospital stay. Also, it would be advantageous to the patient if the time period for recovery is reduced. The invention provides this benefit and these advantages.

OBJECT AND SUMMARY OF THE INVENTION

It is an object of the invention to provide an occlusion apparatus and a method for necrotizing anatomical tissue structures for use as an alternative surgical procedure to a hysterectomy.

Another object of the invention is to provide an occlusion apparatus and a method for necrotizing anatomical tissue structures as an alternative surgical procedure for treatment of a variety of organs, such as a uterus, a gall bladder and a prostate.

Yet another object of the present invention is to provide an occlusion apparatus and a method for necrotizing anatomical tissue structures that result in reduced hospital stay for the patient.

A still further object of the invention is to provide an occlusion apparatus and a method for necrotizing anatomical tissue structures that result in reduced recovery time for the patient.

Accordingly, a method for necrotizing anatomical tissue structures and an occlusion apparatus of the invention are hereinafter described. The method of the invention necrotizes an anatomical tissue structure in a living body. The anatomical tissue structure is connected to a plurality of vessels that extend from the anatomical tissue structure and convey fluids into and out of the anatomical tissue structure. The method of the invention includes locating the anatomical tissue structure to be necrotized and the vessels extending therefrom in the living body. Also, the method of the invention includes occluding the vessels to prevent fluid flow into and out of the anatomical tissue structure to cause ischemic necrosis of the anatomical tissue structure.

The occlusion apparatus of the invention necrotizes the anatomical tissue structure disposed in the living body. The occlusion apparatus of the invention includes an elongated tubular member and an occluding mechanism. The elongated tubular member extends along a central longitudinal axis to define a lumen. The elongated tubular member also has a distal end positioned interiorly of the living body and a proximal end disposed opposite the distal end and positioned exteriorly of the living body.

The occluding mechanism is operative at the distal end of the tubular member and includes a pair of occluding elements disposed opposite one another. The pair of occluding elements are moveable to and between an opened state and a closed state. In the opened state, the vessels to be occluded are received between the pair of occluding elements. In the closed state, the pair of occluding elements contact and occlude the vessels, thereby necrotizing the anatomical tissue structure.

Other objects and advantages of the invention will become apparent from the following description of the embodiments taken in conjunction with the accompanying drawings.

BRIEF DESCRIPTION OF THE DRAWINGS

FIG. 1 is a perspective view of the occlusion apparatus of the invention with facially-opposing occluding end segments in a spaced-apart opened state.

FIG. 2 is a perspective view of the occlusion apparatus of the invention shown in FIG. 1 with the facially-opposing occluding end segments in a contacting closed state.

FIG. 3 is an enlarged partial perspective view of a distal portion of the occlusion apparatus of the invention taken along line 3—3 in FIG. 2.

FIG. 4 is an enlarged partial side view shown partially in cross-section of the occlusion apparatus as shown in FIG. 1.

FIG. 5 is an enlarged partial side view shown partially in cross-section of the occlusion apparatus as shown in FIG. 2.

FIG. 6 is a side view shown partially in cross-section of the occlusion apparatus of the invention shown in FIG. 1.

FIG. 7 is an enlarged partial side view shown partially in cross-section of a proximal end of the occlusion apparatus of the invention.

FIG. 8 is a cross-sectional view of the occlusion apparatus of the invention taken along line 8—8 in FIG. 6.

FIG. 9 is a partial perspective view of an occluding arm member having a flattened occluding end segment.

FIG. 10 is a partial perspective view of an alternative occluding arm member having a flattened, curved occluding end segment.

FIG. 11 is a partial perspective view of an alternative occluding arm member with a tapered section.

DETAILED DESCRIPTION OF THE EXEMPLARY EMBODIMENTS

Figure 17:
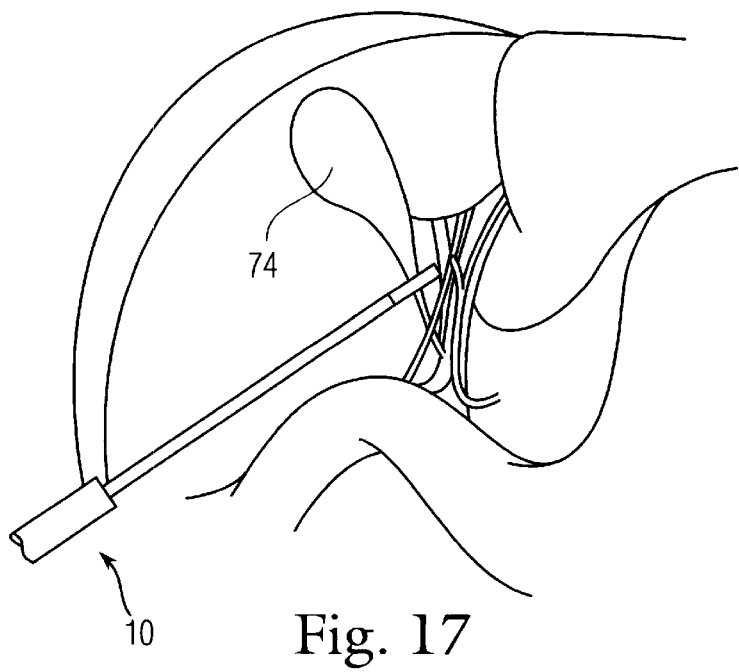
FIG. 17 is a diagrammatic view of the occlusion apparatus of the invention occluding a gall bladder.

An occlusion apparatus of the invention and a method for necrotizing anatomical tissue structures are hereinafter described. The detailed description of the exemplary embodiments describes the invention using anatomical tissue structures such as a uterus, a gall bladder and a prostate. However, one of ordinary skill in the art would appreciate that these anatomical tissue structures are used by way of example only, and that other types of anatomical tissue structures, such as a cystic tumor, a kidney, a pancreas and an ovary, can benefit from the invention. Furthermore, one of ordinary skill in the art would appreciate that even portions of a liver or other organs can be occluded and necrotized as described herein.

An occlusion apparatus 10 of the invention is generally introduced in FIGS. 1–8. The occlusion apparatus 10 of the invention includes an elongated tubular member 12, a pair of occluding arm members 14 and an actuating device 16. The tubular member 12 extends along a central longitudinal axis "A" to define a lumen 18. The tubular member 12 has a distal end 20 and a proximal end 22 which is disposed opposite the distal end 20.

As best shown in FIG. 6, the pair of occluding arm members 14 extend into and through the lumen 18 and project generally longitudinally from the distal end 20 of the tubular member 12 in a facially-opposing relationship. Each one of the pair of occluding arm members 14 terminates in an occluding end segment 24. In cooperation with the pair of occluding arm members 14, each occluding end segment 24 is moveable relative to one another to and between an opened state as shown in FIGS. 1, 4 and 6, and a closed state as shown in FIGS. 2 and 5. In the opened state, the occluding end segments 24 are spaced apart from one another. In the closed state, the occluding end segments 24 contact one another. However, as discussed below, the occluding end segments 24 can be positioned adjacent to one another in the closed state.

As shown in FIGS. 1, 2, 6 and 7, the actuating device 16 is disposed at the proximal end 22 of the tubular member 12. The actuating device 16 is operative in conjunction with the occluding arm members 14 to move the occluding end segments 24 to and between the opened and closed states. Although not by way of limitation, the actuating device 16 are individual finger tabs that extend transversely to the central longitudinal axis "A" as best shown in FIG. 6. Preferably, respective ones of the finger tabs are integrally formed with respective ones of the occluding arm members 14. Further, a skilled artisan would appreciate that other conventional types of actuating devices could be used to move the occluding end segments to and between the opened and closed states.

As best shown in FIGS. 3, 4 and 6, each one of the pair of occluding arm members 14 includes a bent section 28. Thus, the occluding arm members 14 bend outwardly at an acute angle "a" as measured relative to the central longitudinal axis "A." Further, the occluding arm members 14 bend outwardly from the distal end 20 of the tubular member 12 to form a bent condition in respective ones of the occluding arm members 14. The outwardly-bent occluding arm members 14 are resiliently biased in the bent condition to retain the respective occluding end segments 24 in the opened state. Although not by way of limitation, the outwardly-bent occluding arm members 14 are an integral construction fabricated from metal having shape-memory characteristics such as nitinol.

Pulling the actuating device 16 in a direction "D" as shown in FIG. 7 moves the occluding end segments 24 to the closed state (FIGS. 2 and 5) from the opened state (FIGS. 1, 4 and 6). Pulling the actuating device 16 pulls the pair of occluding arm members 14 into the lumen 18 at the bent section 28 thereby pulling the occluding end segments 24 toward the distal end 20 of the tubular member 12. Also, pushing the actuating device 26 opposite to the direction "D" shown in FIG. 7 moves the occluding end segments 24 to the opened state from the closed state. Pushing the actuating device 16 also pushes the pair of occluding arm members 14 outwardly from the lumen 18 thereby pushing the occluding end segments 24 away from the distal end 20 of the tubular member 12.

In FIGS. 1 and 3–6, each one of the pair of occluding arm members 14 includes a protuberance 30. Each respective protuberance 30 is disposed adjacent the bent section 28. Also, each respective protuberance 30 is disposed exteriorly of the lumen 18 when the occluding end segments 24 are in the open state. Also, the respective protuberances 30 contact the distal end 20 of the tubular member 12 within the lumen 18 when the occluding end segments 24 are in the closed state.

The occlusion apparatus 10 of the invention also includes an inner tubular member 32 that is disposed within the lumen 18 of the tubular member 12. The inner tubular member 32 defines a central operating channel 34 interiorly of the inner tubular member 32 and an annular channel 36 that is formed between the tubular member 12 and the inner tubular member 32. In other words, with the inner tubular member 32 disposed within the tubular member 12, the lumin 18 is divided into the central operating channel 34 and the annular channel 36 disposed about the operating channel 34. As shown in FIGS. 1–6, the pair of occluding arm members 14 are disposed within the annular channel 36.

Further, the occlusion apparatus 12 of the invention includes a frame structure 38 as best shown in FIGS. 3 and 6. The frame structure 38 includes a plurality of spacers 40 interconnected by a plurality of spacer bars 42. The frame structure 38 retains the inner tubular member 32 centrally about the central longitudinal axis "A." Also, as best shown in FIG. 3, each spacer 40 has a pair of guide holes 44. Each guide hole 44 is sized and adapted to slideably receive a respective one of the occluding arm members 14. The spacers 40 and guide holes 44 provide support and proper alignment of the occluding arm members 14.

As shown in FIGS. 4 and 5, the pair of occluding end segments 24 extend parallel to respective longitudinal axes "L." When the occluding end segments 24 are in the closed state, the respective ones of the longitudinal axes "L" extend parallel to the central longitudinal axis "A."

In FIGS. 4 and 5, an opening 46 is formed exteriorly of the distal end 20 of the tubular member 12 and between the pair of occluding arm members 14 for receiving anatomical tissue. When the occluding end segments 24 are in the opened state (FIG. 4), the respective ones of the longitudinal axes "L" are disposed at the acute angle "a" relative to the central longitudinal axis "A."

In FIG. 1, the occlusion apparatus 10 of the invention also includes a viewing system 48 and an energy source 50. As is known in the art, the viewing system 48 includes a viewing member (not shown) which is sized and adapted to be slideably received by operating channel 34 of the inner tubular member 32. Alternatively, the inner tubular member 32 itself could be the viewing member. For the occlusion apparatus shown in FIG. 1, respective ones of the occluding end segments 24 are a pair of heating elements configured with a triangular cross-section. The energy source 50 is connected to terminals 52 to supply either electric energy, ultrasonic energy or laser energy to the pair of heating elements, particularly at the apex of each occluding end segment 24.

The occluding end segments 24 can have other configurations. In FIG. 9, the occluding end segment 24 has a generally flattened, rectangular shape. In FIG. 10, the occluding end segment 24 is arcuate.

Figure 12:
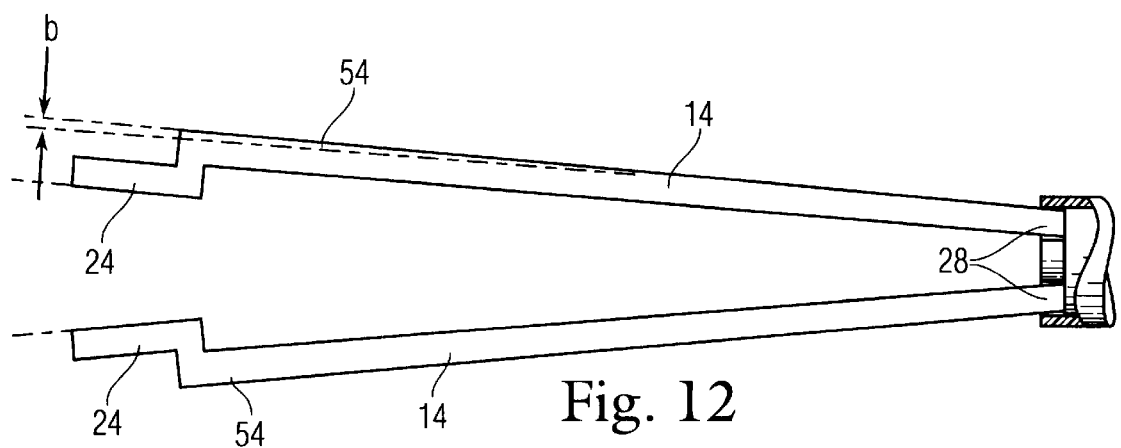
FIG. 12 is a side view, partially in cross-section, with the occluding end segments connected to respective tapered sections and being in the opened state.
Figure 13:
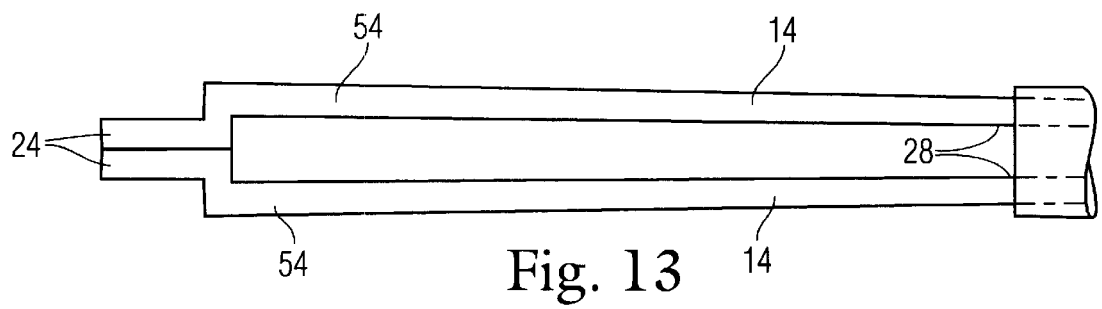
FIG. 13 is a side view, partially in cross-section, with the occluding end segments connected to respective tapered sections and being in the closed state.

In FIGS. 11–13, each one of the pair of occluding arm members 14 includes a tapered section 54 rather than a protuberance 30. The tapered section 54 extends approximately between the occluding end segment 24 and the bent section 28. The tapered section 54 narrows at an angle "b" from the occluding end segment 24 towards the bent section 28. Like the protuberance 30, the tapered section 54 assists in moving the occluding end segments 24 from the opened state to the closed state.

Figure 14:
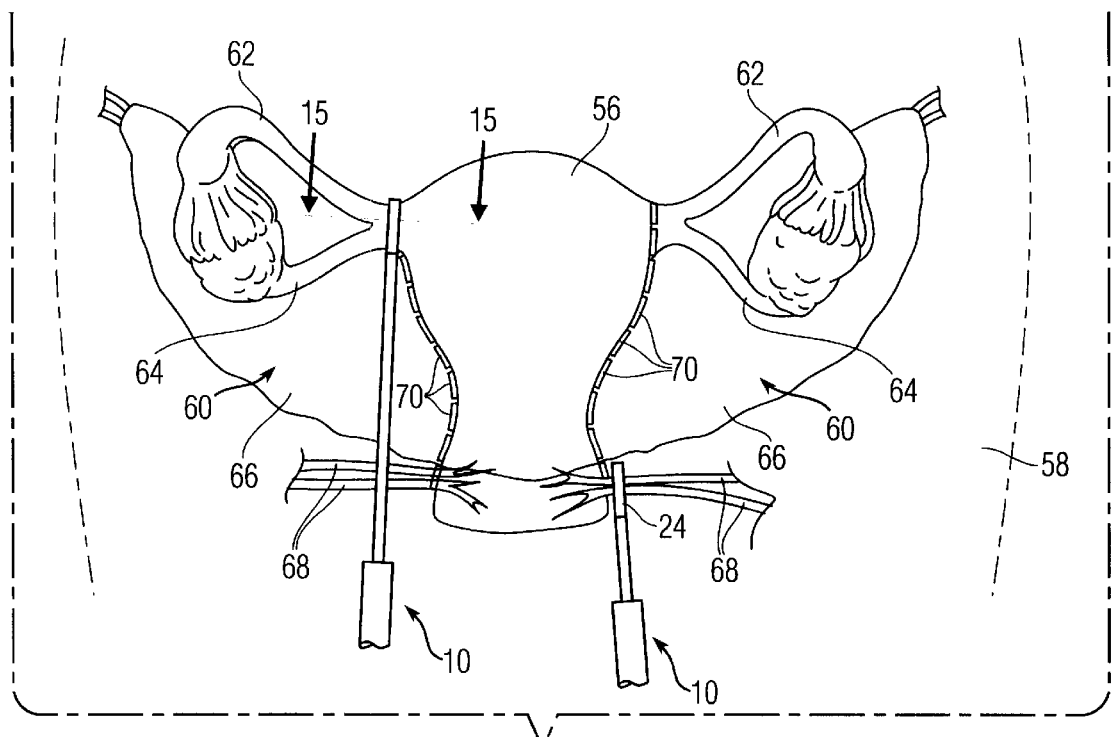
FIG. 14 is a diagrammatic view illustrating a pair of occlusion apparatuses of the invention with occluding end segments occluding vessels of a uterus.

The occlusion apparatus 10 of the invention is particularly useful for necrotizing an anatomical tissue structure such as a uterus 56. As shown in FIG. 14, the uterus 56 is disposed in a living body 58. The anatomical tissue structure has a plurality of vessels that extend therefrom. As is known in the art, the uterus 56 is connected to and between a pair of ligamentous tissue structures 60 in the living female body 58. Generally, the ligamentous tissue structure 60 includes a pair of fallopian tubes 62, a pair of round ligaments 64, a pair of broad ligaments 66 and uterine vessels 68. A skilled artisan would appreciate that the ligamentous tissue structure 60 also includes a pair of ovarian ligaments (not shown,) a pair of uterosacral ligaments and other tissues structures. The uterine vessels 68 are occluded adjacent the uterus 56 to cause ischemic necrosis of the uterus 56. As shown in FIG. 14, the occluding apparatus 10 of the invention is used for cauterizing the ligamentous tissue structure 60 adjacent the uterus 56. Specifically, cauterized segments 70 are formed adjacent the uterus 56 on the fallopian tubes 62, the round ligaments 64, the broad ligaments 66 as well as the uterine vessels 68. However, a skilled artisan would appreciate that the uterine vessels 68 should be cauterized first and cauterization of the left and right ureters must be avoided.

Figure 15:
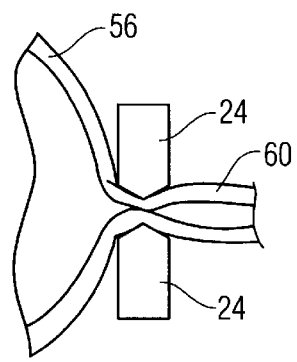
FIG. 15 is an enlarged partial side view of the occluding end segments occluding a vessel as taken along line 15—15 in FIG. 14.

FIG. 15 illustrates the pair of occluding end segments 24 contacting and compressing the ligamentous tissue structure 60 and heating the same to achieve cauterization. However, occluding the ligamentous tissue structure 60 occurs without severing either one the ligamentous tissue structures 60. Thus, the uterus is still connected to the ligamentous tissue structure 60 even after performing the occlusion procedure. As a result of the occlusion procedure, the anatomical tissue structure, which in this case is the uterus 56, is rendered non-functional in situ.

Figure 16:
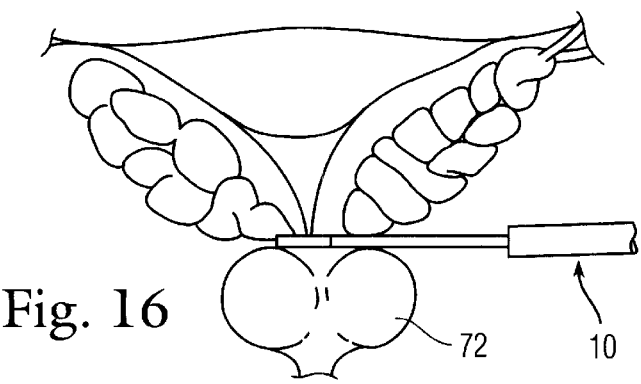
FIG. 16 is a diagrammatic view of the occlusion apparatus of the invention occluding vessels of a prostate.

As stated above, the occlusion apparatus 10 of the invention can be used with a variety of anatomical tissue structures. In FIG. 16, the occlusion apparatus 10 of the invention is used for occluding vessels connected to a prostate 72. In FIG. 17, the occlusion apparatus 10 of the invention is used for occluding vessels connected to a gall bladder 74.

For the occlusion apparatus 10 of the invention discussed above, it is appreciated that the occluding mechanism includes the energy source 50 and the pair of occluding end segments 24 which operate as a pair of occluding elements. The energy source 50 is operative in conjunction with the pair of occluding elements to generate heat sufficient to cauterize (but not severe) the vessels, thereby necrotizing the anatomical tissue structure connected thereto. For the occlusion apparatus 10 of the invention, the energy source 50 can be electrical energy, ultrasound energy, laser energy or the like. A skilled artisan would appreciate that other occluding mechanisms can be used.

Figure 18:
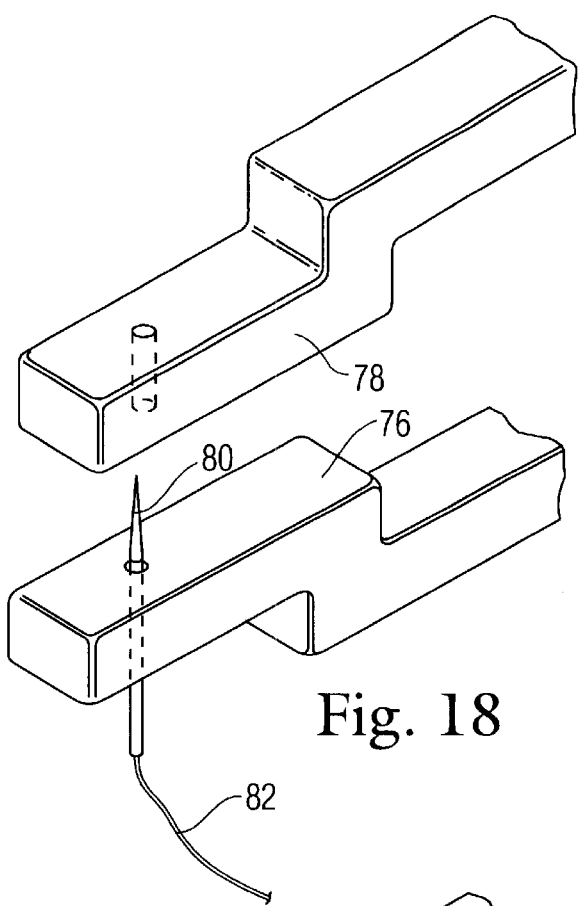
FIG. 18 is a perspective view of the occluding end segments used with a representative needle and suture device.
Figure 19:
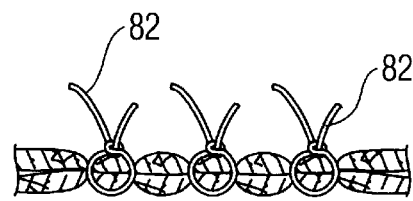
FIG. 19 is a side elevational view of anatomical tissue occluded by tied sutures.

In FIG. 18, the occluding elements include a needle passer 76 and a needle catcher 78. Also, the occluding mechanism includes a needle 80 and a suture 82 connected to the needle 80. The needle passer 76 holds the needle 80 and suture 82 when the pair of occluding elements are in the open state. The needle catcher 78 catches the needs 80 when the pair of occluding elements are in the closed state. In FIG. 19, after the needle 80 and suture 82 are passed through vessels extending from anatomical tissue to be necrotized, the sutures 82 are tied. Thus, occlusion is achieved by suturing at least the vessels without severing the same.

Figure 20:
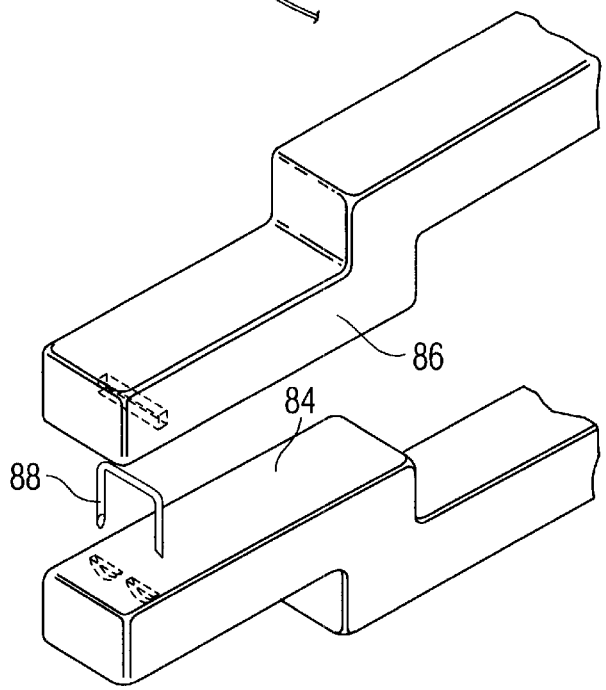
FIG. 20 is an enlarged partial perspective view of the pair of occluding end segments used and represented as an anvil and stapler device.
Figure 21:
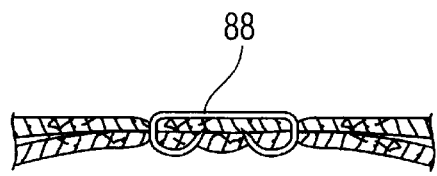
FIG. 21 is a side elevational view of anatomical tissue occluded by a staple.

In FIG. 20, the occluding mechanism includes a pair of occluding elements in the form of an anvil 84 a staple holder 86 and a staple 88. In conjunction with the anvil 84 and the staple holder 86, the staple 88 moves between a pre-stapled condition (FIG. 20) and a stapled condition (FIG. 21). The staple 88 is carried by the staple holder 86 in the pre-stapled condition when the pair of occluding elements are in the opened state. The occluding mechanism is operative because the staple 88 moves from the pre-stapled condition to the stapled condition when the pair of occluding elements move to the closed state. The staple 88 in the stapled condition occludes the vessels thereby necrotizing the anatomical tissue structure. Thus, occlusion is also achieved by stapling without severing the anatomical tissue structure.

Figure 22:
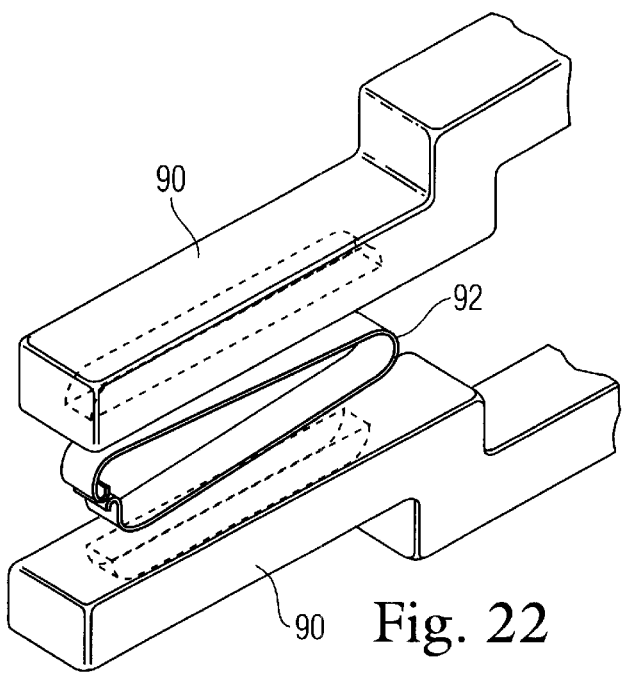
FIG. 22 is an enlarged partial perspective view of the pair of occluding end segments used represented in combination with a conventional clamp.
Figure 23:
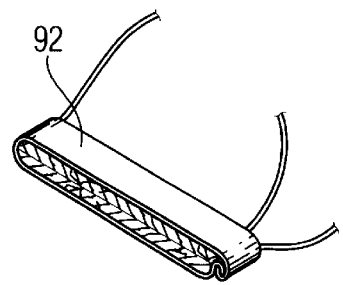
FIG. 23 is a side elevational view of the clamp occluding anatomical tissue.

In FIGS. 22 and 23, the occluding mechanism includes a pair of occluding elements in a form of a pair of clamping members 90 and a clamp 92. Although not by way of limitation, at least one of the pair of clamping members 90 include a recess 94 that is sized and adapted for receiving and releasably holding the clamp 92. The clamp 92 moves from an opened condition (FIG. 22) to a closed condition (FIG. 23). The pair of occluding elements are configured to releaseably retain the clamp 92 in the opened condition so that the clamp 92 receives the vessels to be occluded. The pair of occluding elements are configured also to cause the clamp 92 to move to the closed condition to occlude the vessels, thereby necrotizing the anatomical tissue structure. Thus, occlusion is achieved by clamping without severing the anatomical tissue structure.

Figure 24:
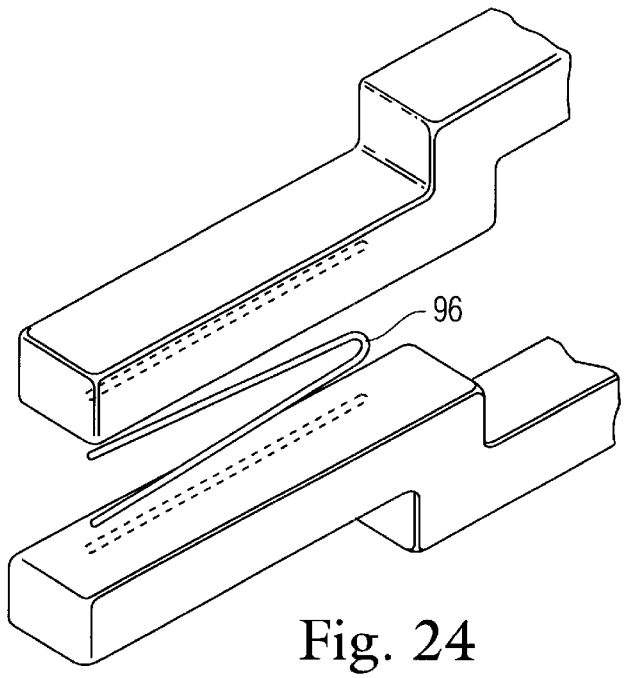
FIG. 24 is an enlarged partial perspective view of the pair of occluding end segments used with a conventional clip.
Figure 25:
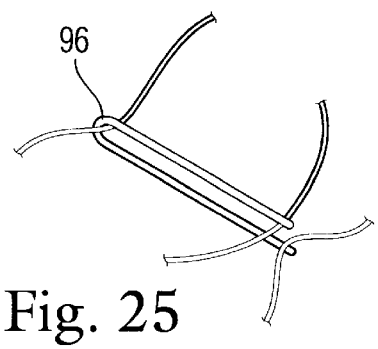
FIG. 25 is a perspective view of the clip occluding a vessel.

In FIGS. 24 and 25, the occluding mechanism includes a pair of occluding elements in a form of a pair of clamping members 90 which are similar to those discussed above. The occluding mechanism also includes a generally U-shaped clip 96 that moves from an opened condition to a closed condition. The pair of occluding elements are configured to releaseably retain the clip 96 in the opened condition so that the clip 96 receives the vessels to be occluded. The pair of occluding elements are configured also to cause the clip 96 to move to the closed condition (FIG. 25) to occlude the vessels, thereby necrotizing the anatomical tissue structure. Thus, occlusion is achieved by clipping without severing the anatomical tissue structure.

Note that none of the occluding mechanisms described result in severing the vessels. The anatomical tissue structure in each instance is necrotized without severing the vessels that are connected to them.

Another embodiment of the invention is a method for necrotizing an anatomical tissue structure in a living body. The anatomical tissue structure is connected to a plurality of vessels that extend from the anatomical tissue structure and convey fluids into and out of the anatomical tissue structure. The method includes locating the anatomical tissue structure to be necrotized and the vessels extending therefrom in the living body. A next step is occluding the vessels to prevent fluid flow into and out of the anatomical tissue structure to cause ischemic necrosis of the anatomical tissue structure.

In some instances, a tissue mass is connected to the anatomical tissue structure and supports the vessels extending from the anatomical tissue structure. As discussed above, by way of example only, the tissue mass can be the ligamentous tissue structure that supports the uterus and vessels extending therefrom. The vessels can be either embedded in the tissue mass or disposed on a surface of the tissue mass. The tissue mass itself, along with the vessels, can be occluded by cauterizing, stapling, clamping, clipping or suturing. The anatomical tissue structure is typically defined by an outer surface. Preferably, the step of occluding the vessels occurs adjacent the outer surface of the anatomical tissue structure. Preferably, the vessels include at least one blood-conveying artery and at least one blood-conveying vein. Such blood-conveying artery and blood-conveying vein are illustrated by way of example, only, in FIG. 14 as uterine vessels 68.

Practicing the occlusion apparatus and method for necrotizing an anatomical tissue structure of the invention avoids removal of the anatomical tissue structure from the living body. Also, minimal invasive surgery techniques can be used to practice the invention. Benefits of practicing the invention include less hospital stay and less recovery time for the patient.

Although the embodiments of the invention have been specifically described herein, it would be apparent to those skilled in the art to which the invention pertains that other variations and modifications of the embodiments herein may be made without departing from the spirit and scope of the invention.

What is claimed is:

1. A method for necrotizing an anatomical tissue structure in a living body, the anatomical tissue structure connected to a plurality of vessels extending from the anatomical tissue structure and conveying fluids into and out of the anatomical tissue structure, the method comprising the steps of:

locating the anatomical tissue structure to be necrotized and the vessels extending therefrom in the living body; and occluding the vessels to prevent fluid flow into and out of the anatomical tissue structure to cause ischemic necrosis of the anatomical tissue structure;

whereby said method avoids severing vessels or removing said anatomical tissue structure.

2. A method according to claim 1, wherein the step of occluding occurs without severing the vessels.

3. A method according to claim 1, wherein a tissue mass is connected to the anatomical tissue structure and supports the vessels extending from the anatomical tissue structure.

4. A method according to claim 3, wherein the vessels are embedded in the tissue mass.

5. A method according to claim 4, wherein the step of occluding is achieved by one of cauterizing, stapling, clamping, clipping and suturing.

6. A method according to claim 1, wherein the anatomical tissue structure is defined by an outer surface and the step of occluding occurs adjacent the outer surface.

7. A method according to claim 1, wherein the step of occluding is achieved by one of cauterizing, stapling, clamping, clipping and suturing.

8. A method according to claim 7, wherein the anatomical tissue structure is defined by an outer surface and the step of occluding occurs adjacent the outer surface.

9. A method according to claim 1, wherein the anatomical tissue structure is one of a uterus, a gallbladder and a prostate.

10. A method according to claim 1, wherein the plurality of vessels includes at least one blood-conveying artery and at least one blood-conveying vein.

11. A method for necrotizing a uterus in a living female body, the uterus supported in the living female body by a pair of laterally-extending ligamentous tissue structures connected with a plurality of vessels extending into and from the uterus, the method comprising the steps of locating the uterus and the pair of ligamentous tissue structures in the living female body; and occluding the extending vessels adjacent the uterus to cause ischemic necrosis of the uterus;

whereby said method avoids severing vessels or removing said uterus.

12. A method according to claim 11, wherein the step of occluding is achieved by one of cauterizing, stapling, clamping, clipping and suturing at least the vessels.

13. A method according to claim 11, wherein the step of occluding occurs without severing either the ligamentous tissue structures or the vessels.

14. A method according to claim 11, wherein each of the ligamentous tissue structures includes a fallopian tube, a round ligament, a broad ligament, and uterine vessels.

* * * * *